United States Patent [19]

Bowler et al.

[11] 4,004,021
[45] Jan. 18, 1977

[54] CYCLOPENTANE DERIVATIVES

[75] Inventors: Jean Bowler; Edward Douglas Brown; Peter Robert Marsham; Edward Raymond Halstead Walker, all of Macclesfield, England

[73] Assignee: Imperial Chemical Industries Limited, London, England

[22] Filed: Dec. 18, 1975

[21] Appl. No.: 641,871

Related U.S. Application Data

[62] Division of Ser. No. 434,303, Jan. 17, 1974.

[30] Foreign Application Priority Data

Jan. 31, 1973 United Kingdom ............... 4769/73

[52] U.S. Cl. .................. 424/278; 424/248.55; 424/275; 424/283; 424/285; 424/298; 424/305; 424/248.53; 260/240 R; 260/244 R; 260/330.5; 260/340.5; 260/340.7; 260/345.5; 260/346.2 R; 260/468 D; 260/473 A; 260/514 D; 260/520 B; 424/248.57
[51] Int. Cl.² ......................................... C07D 307/78
[58] Field of Search ............... 260/240 R, 346.2 R; 424/278

[56] References Cited

UNITED STATES PATENTS 3,678,092   7/1972   Finch ........................... 260/468 D

FOREIGN PATENTS OR APPLICATIONS

| 786,251 | 1/1973 | Belgium | 260/468 D |
| 799,048 | 5/1973 | Belgium | 260/468 D |
| 805,358 | 3/1974 | Belgium | 260/520 B |
| 807,046 | 8/1974 | Belgium | 260/520 B |

OTHER PUBLICATIONS

Chemical Abstracts, vol. 77, abst. No. 74,887f, (abst. of German Offen. 2,154,309), 1972.

*Primary Examiner*—John D. Randolph
*Attorney, Agent, or Firm*—Cushman, Darby & Cushman

[57] ABSTRACT

The disclosure relates to novel pentanor prostaglandin analogues, for example 15-(5-chloroindan-2-yl)-9α,1-1α,15-trihydroxy-16,17,18,19,20-pentanor-5-cis,13-trans-prostadienoic acid and 15-(5-chloroindan-2-yl)-11α,15-dihydroxy-9-oxo-16,17,18,19,20-pentanor-5-cis,13-trans-prostadienoic acid and the 1-ester and 1-alcohol derivatives thereof, to a process for their manufacture, to compositions containing them, and to their use in a method of inducing luteolysis.

7 Claims, No Drawings

CYCLOPENTANE DERIVATIVES

This invention relates to new cyclopentane derivatives, and in particular it relates to new cyclopentane derivatives which are analogues of the naturally occurring compounds known as prostaglandin $F_2\alpha$ and prostaglandin $E_2$, showing a similar spectrum of pharmacological properties and being useful for similar purposes. The relative potency of the new compounds, however, in respect of the particular pharmacological effects shown is different from that of the above naturally occurring prostaglandins, and in particular they are more potent as luteolytic agents than the corresponding natural prostaglandins. That is to say, in general the prostaglandin $F_2\alpha$ analogues of the present invention are more potent than natural prostaglandin $F_2\alpha$, and the prostaglandin $E_2$ analogues of the present invention are more potent than natural prostaglandin $E_2$. The new compounds are, however, less potent as stimulants of uterine smooth muscle than the corresponding natural prostaglandins $F_2\alpha$ and $E_2$, and are therefore more selective in respect of luteolytic activity than the natural prostaglandins. The new compounds are therefore advantageous when used as contraceptives, for the termination of pregnancy or for control of the oestrus cycle, and are also useful as hypotensives or for the relief of bronchospasm, and as inhibitors of blood platelet aggregation or of gastric secretion. The new compounds of the invention are also useful for addition to semen intended for artificial insemination of domestic animals, the success rate of insemination being thereby increased, especially in pigs and cattle.

According to the invention there is provided a

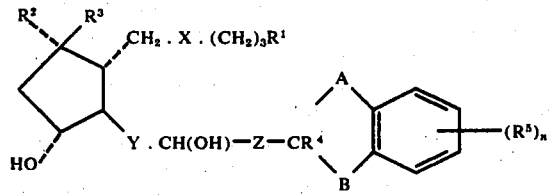

wherein $R_1$ is a carboxy or hydroxymethyl radical, or an alkoxycarbonyl radical of up to 11 carbon atoms; either $R^2$ is a hydroxy radical or an alkanoyloxy radical of 1 to 4 carbon atoms, and $R^3$ is a hydrogen atom, or $P^2$ and $R^3$ together form an oxo radical; X is an ethylene or cis-vinylene radical; Y is an ethylene or trans-vinylene radical Z is a direct bond or an alkylidene radical of 1 to 5 carbon atoms; either A is an alkylidene radical of 1 to 5 carbon atoms or an ethylene radical, and B is a direct bond, an oxygen or sulphur atom, or an alkylidene radical of 1 to 5 carbon atoms, or A is an oxygen atom and B is an oxygen atom, an alkylideneoxy radical of 1 to 5 carbon atoms wherein the oxygen atom is linked directly to the benzene ring, or an alkylidene(alkylimino) radical [alkylidene-N(alkyl)-] wherein the alkylidene radical is of 1 to 5 carbon atoms and the alkyl radical is of 1 to 4 carbon atoms, and wherein the nitrogen atom is linked directly to the benzene ring; $R_4$ is a hydrogen atom or an alkyl radical of 1 to 4 carbon atoms, or $CR^4$ together with an adjacent carbon atom of A or B forms a double bond; $R^5$ is a halogen atom, or an alkyl, alkoxy or halogenoalkyl radical of 1 to 3 carbon atoms, and $n$ is 0, 1 or 2; which compound bears 0 or 1 alkyl substituent of 1 to 4 carbon atoms on the trimethylene [$-(CH_2)_3-$] group; and for those compounds wherein $R^1$ is the carboxy radical, the pharmaceutically- or veterinarily-acceptable base addition salts thereof.

A suitable value for $R^1$ when it is an alkoxycarbonyl radical of up to 11 carbon atoms is, for example, a methoxycarbonyl, ethoxycarbonyl, propoxycarbonyl, butoxycarbonyl, pentyloxycarbonyl, hexyloxycarbonyl octyloxycarbonyl, or decyloxycarbonyl radical, preferably straight chain such radicals.

A suitable value for $R^2$ when it is an alkanoyloxy radical of 1 to 4 carbon atoms is, for example, an acetoxy or propionyloxy radical.

A suitable value for A or B when it is an alkylidene radical of 1 to 5 carbon atoms is, for example, a methylene, ethylidene, propylidene or butylidene radical. A suitable value for B when it is an alkylideneoxy radical of 1 to 5 carbon atoms is, for example a methyleneoxy, ethylideneoxy or propylideneoxy radical, and a suitable value for B when it is an alkylidene(alkylimino) radical is for example a methylene(methylimino), [$-CH_2N(CH_3)-$]radical.

A suitable value for Z when it is an alkylidene radical of 1 to 5 carbon atoms is, for example, a methylene, ethylidene or propylidene radical.

A suitable value for $R^4$ when it is an alkyl radical of 1 to 4 carbon atoms is, for example, a methyl or ethyl radical.

A suitable value for $R^5$ when it is a halogen atom is, for example, the chlorine, bromine, iodine or fluorine atom. A suitable value for $R^5$ when it is an alkyl or alkoxy radical of 1 to 3 carbon atoms is, for example, a methyl, ethyl, methoxy or ethoxy radical, and a suitable value when it is a halogenoalkyl radical of 1 to 3 carbon atoms is, for example, a trihalogenomethyl radical, for example the trifluoromethyl radical.

A suitable value for the alkyl substituent on the trimethylene group is, for example a methyl or ethyl radical. Possible values for the radical:

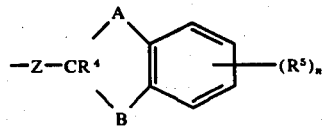

are therefore, the 1-benzocyclobutanyl, 1-benzocyclobutenyl, 1-indanyl, 2-indanyl, 2-indanylmethyl, 2-(2-indanyl)ethyl, 1,2,3,4-tetrahydro-2-naphthyl, 2-chromanyl, 2-indenyl, benzo[1,3]dioxol-2-yl, 2-benzo[b]furyl, 2,3-dihydrobenzo[b]-fur-2-yl, 2- and 3-benzo[b]thienyl, 2,3-dihydrobenzo[b]thien-2-yl, benzo[1,4]dioxan-2-yl and benzomorpholin-2-yl radicals, optionally substituted as defined above.

Particular values for the radical:

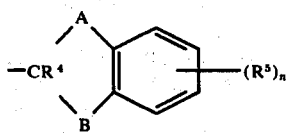

wherein $n$ is 1 or 2 are 5-chloroindan-2-yl, 5,6-dichloroindan-2yl, 5-methylindan-2-yl, 5-chlorobenzo[b]fur-2-yl, 5-chloro-2-methylbenzo[b]fur-2-yl, 5-methoxybenzo[b]fur-2-yl and 6-methoxybenzo[b]fur-2-yl radicals.

A suitable pharmaceutically- or veterinarily-acceptable base addition salt is, for example the ammonium, alkyl-ammonium containing 1 to 4 alkyl radicals each of 1 to 6 carbon atoms, alkanolammonium containing 1 to 3 2-hydroxyethyl radicals, or alkali metal salt, for example the triethylammonium, ethanolammonium, diethanolammonium, sodium, potassium or ammonium salt.

It will be observed that the compounds of the formula I contain at least five asymmetric carbon atoms, namely carbon atoms 8, 9, 11, 12 and 15, the configurations at four of which, 8, 9, 11 and 12 are specified in formula I, and that carbon atoms 2,3,4 and 16 may also be asymmetrically substituted, so that it is clear that such compounds can exist in at least two optically active forms. It is to be understood that the useful properties of the racemate may be present to differing extents in the optical isomers, and that this invention relates to the racemic form of the compounds of formula I and any optically active form which shows the above useful properties, it being a matter of common general knowledge how the optically active forms may be obtained, and to determine their respective biological properties.

It is also to be understood that the above definition encompasses both C-15 epimers, and that the terms "more polar" and "less polar" epimers, as applied hereinafter to compounds wherein C-16 is asymmetric, each relate to a pair of diastereoisomers.

A preferred group of cyclopentane derivatives of the invention comprises compounds of the formula:

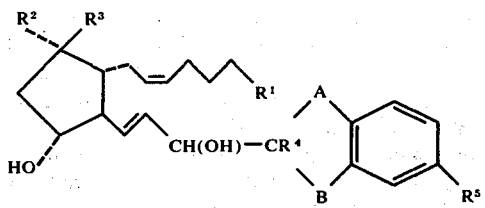

wherein $R^1$ is a carboxy, methoxycarbonyl or hydroxymethyl radical, $R^2$ is a hydroxy radical and $R^3$ is a hydrogen atom or $R^2$ and $R^3$ together form an oxo radical, $R^4$ is a hydrogen atom or a methyl radical, especially a hydrogen atom, A is an oxygen atom or a methylene radical, B is a methylene radical, and $R^5$ is a hydrogen, chlorine or bromine atom, especially hydrogen or chlorine, or a methyl radical, and for those compounds wherein $R^1$ is a carboxy radical, the pharmaceutically- or veterinarily-acceptable base addition salts thereof as defined above.

Particular preferred compounds of the invention are 15-(5-chloroindan-2-yl)-9α,11α,15-trihydroxy-16,17,18,19,20-pentanor-5-cis,13-trans-prostadienoic acid, methyl 15-(5-chloroindan-2-vl)-9α,11α,15-trihydroxy-16,17,18,19,20-pentanor-5-cis,13-trans-prostadienoate, 15-(5-chloroindan-2-yl)-16,17,18,19,20-pentanor-5-cis,13-trans-prostadien-1,9α,11α,15-tetraol, 15-(5-chloro-2,3-dihydrobenzo[b]fur-2-yl)-9α,11α,15-trihydroxy-16,17,18,19,20-pentanor-5-cis,13-trans-prostadienoic acid, 9α,11α-15-trihydroxy-15-(2-methylindan-2-yl)-16,17,18,19,20-pentanor-5-cis,13-trans-prostadienoic acid, 9α,11α,15-trihydroxy-15-(5-methylindan-2-yl)-16,17,18,19,20-pentanor-5-cis,13-trans-prostadienoic acid, 9α,11α,15-trihydroxy-15-(2-indanyl)-16,17,18,19,20-pentanor-5-cis,13-trans-prostadienoic acid and 15-(5-chloro-2,3-dihydro-benzo[b]-fur-2-yl)-11α,15-dihydroxy-9-oxo-16,17,18,19,20-pentanor-5-cis,13-trans-prostadienoic acid.

The cyclopentane derivative of the invention may be manufactured by methods known in themselves for the manufacture of chemically analogous compounds. Thus, the following processes for the manufacture of the cyclopentane derivative of the formula I are provided as further features of the invention:

a. for those compounds wherein $R^1$ is a carboxy radical, the hydrolysis of a compound of the formula:

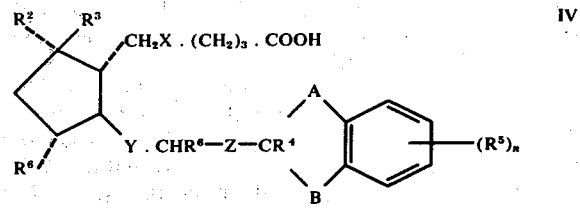

or of a mixed anhydride thereof, wherein A,B,$R^2$,$R^3$,$R^4$, $R^5$, $n$,X,Y and Z have the meanings defined above, and $R^6$ is a tetrahydropyran-2-yloxy radical or an acyloxy radical of 1 to 6 carbon atoms, and bearing 0 or 1 alkyl substituent of 1 to 4 carbon atoms on the trimethylene group, whereafter if a salt is required the product so obtained is reacted with a base; or b. for those compounds wherein $R^1$ is an alkoxycarbonyl radical of up to 11 carbon atoms, the reaction of an acid of the formula I wherein $R^1$ is a carboxy radical, with a diazoalkane of up to 10 carbon atoms, or of a salt thereof, for example the sodium or silver salt with an alkyl halide of up to 10 carbon atoms, for example the alkyl iodide; or c. for those compounds wherein $R^1$ is an alkoxycarbonyl radical of up to 11 carbon atoms, the reaction of an acid of the formula IV, wherein A,B,$R^2$, $R^3$, $R^4$, $R^5$,n,X,Y and Z have the meanings stated above and $R^6$ is a tetrahydropyran-2-yloxy radical and bearing 0 or 1 alkyl substituent of 1 to 4 carbon atoms on the trimethylene group, with an alkanol of 1 to 10 carbon atoms in the presence of a strong acid, for example toluene-p-sulphonic acid, whereafter if the corresponding carboxylic acid is required, the ester so obtained is hydrolysed, for example with potassium hydroxide; or d. for those compounds wherein $R^1$ is a hydroxymethyl radical, the reduction of an ester of the formula I wherein $R^1$ is an alkoxycarbonyl radical, for example an alkoxycarbonyl radical of up to 11 carbon atoms, with a complex metal hydride, for example lithium aluminium hydride; or e. for those compounds wherein $R^1$ is a carboxy radical, $R^2$ is a hydroxy radical and $R^3$ is a hydrogen atom, the reaction of a lactol of the formula:

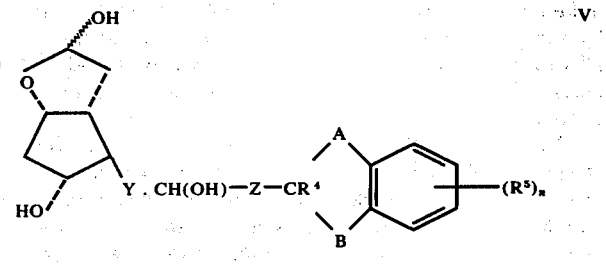

wherein A, B, $R^4$, $R^5$, n, Y and Z have the meanings defined above, with a (4-carboxybutyl)triphenylphosphonium salt, for example the bromide, bearing 0 or 1 alkyl substituent of 1 to 4 carbon atoms on the trimethylene group, in the presence of a strong base, whereafter if a salt is required the product so obtained is reacted with a base; or f. the reduction of a compound of the formula:

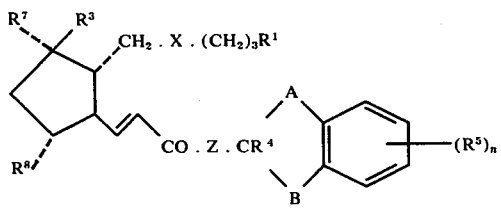

VI wherein $R^1$, $R^3$, $R^4$, $R^5$, A, B, X, Z and n have the meanings stated above and $R^7$ and $R^8$ are each a hydroxy or protected hydroxy radical, and which bears 0 or 1 alkyl substituent of 1 to 4 carbon atoms on the trimethylene group, for example with zinc borohydride, aluminium tri-isopropoxide or di-isobornyloxy aluminium isopropoxide, whereafter when $R^7$ and $R^8$ are each a protected hydroxy radical the protecting groups are removed and if a salt is required, a product so obtained wherein $R^1$ is a carboxy group is reacted with a base; or g. for those compounds wherein $R^2$ is a hydroxy radical and $R^3$ is a hydrogen atom, the reduction, for example with a complex metal hydride, for example a lithium tri(lower alkyl)aluminium hydride such as lithium tri-s-butyl aluminium hydride, or a borohydride, for example sodium borohydride, of the corresponding compound wherein $R^2$ and $R^3$ together form an oxo radical.

A suitable mixed anhydride is a mixed anhydride with a lower alkanoic acid, for example a lower alkanoic acid of up to 8 carbon atoms, for example acetic acid, and a suitable phosphonium salt is, for example, the bromide.

The hydrolysis in process (a) may be carried out under either acidic or basic conditions, for example in aqueous acetic acid, when $R^6$ is a tetrahydropyranyl radical, or in an aqueous or alcoholic solution of an alkali metal carbonate, for example potassium carbonate in methanol, when $R^6$ is an acyloxy radical, and it may be carried out at ambient temperature or at an elevated temperature of up to 60° C.

The starting material of the formula IV, wherein X is a cis-vinylene radical and Y is a trans-vinylene radical, $R^2$ is a hydroxy radical and $R^3$ is a hydrogen atom, may be obtained by reaction of the known aldehyde VII (Ac = acetyl or p-phenylbenzoyl) with a phosphonate of the formula $(CH_3O)_2PO.CH_2CO.ZR^9$ wherein $R^9$ is

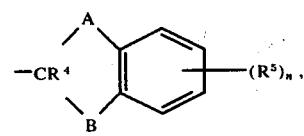

(which is prepared from dimethyl methylphosphonate and an ester $R^9.Z.COOAlkyl$) in the presence of a strong base, or with a phosphorane of the formula $R^9Z.CO.CH:PPh_3$ (which is prepared, for example, from triphenylphosphine and a compound of the formula $R^9.Z.CO.CH_2I$), to give an enone VIII. The enone VIII is reduced with zinc borohydride or an aluminium tri-isopropoxide, to the corresponding enol IX, and the protecting acyl group is then removed with potassium carbonate in methanol to give a diol X. The diol X is either reduced with di-isobutyl aluminium hydride to the lactol starting material of the

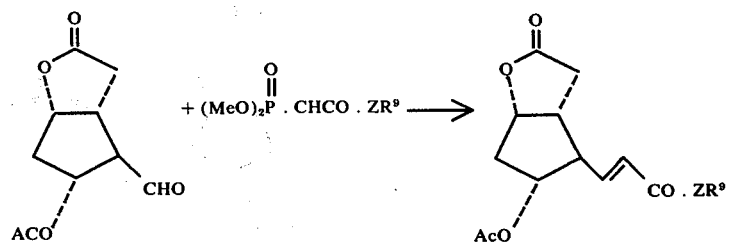

VII　　　　　　　　　　VIII

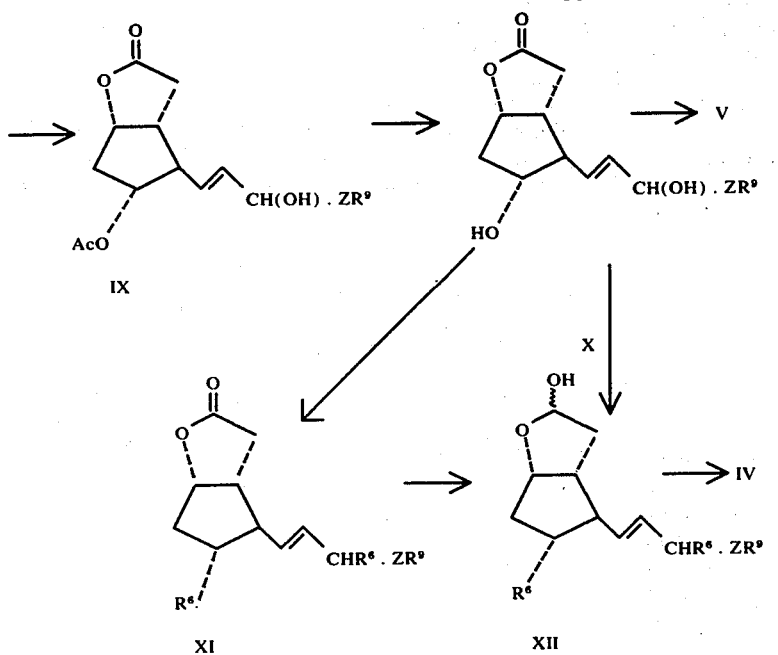

Ac represents an acetyl or p-phenylbenzoyl radical.

formula V, or is protected as a bis-tetrahydropyranyl ether XI and the lactone ring is then reduced with di-isobutyl aluminium hydride to give a lactol XII ($R^6=$ tetrahydropyran-2-yloxy). Alternatively, the diol X is reduced directly with di-isobutyl aluminium hydride to give a triol which may be acylated and selectively hydrolysed to give the lactol bis-ester (XII, $R^6=$ acyloxy). A lactol XII is reacted with the phosphonium ylide anion obtained from (4-carboxybutyl) triphenyl-phosphonium bromide and a strong base, to give a carboxylic acid of the formula IV.

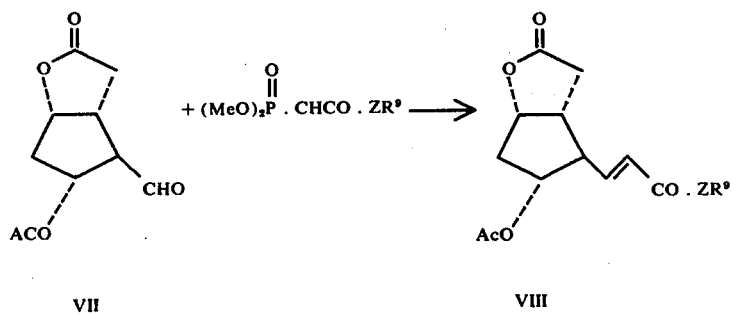

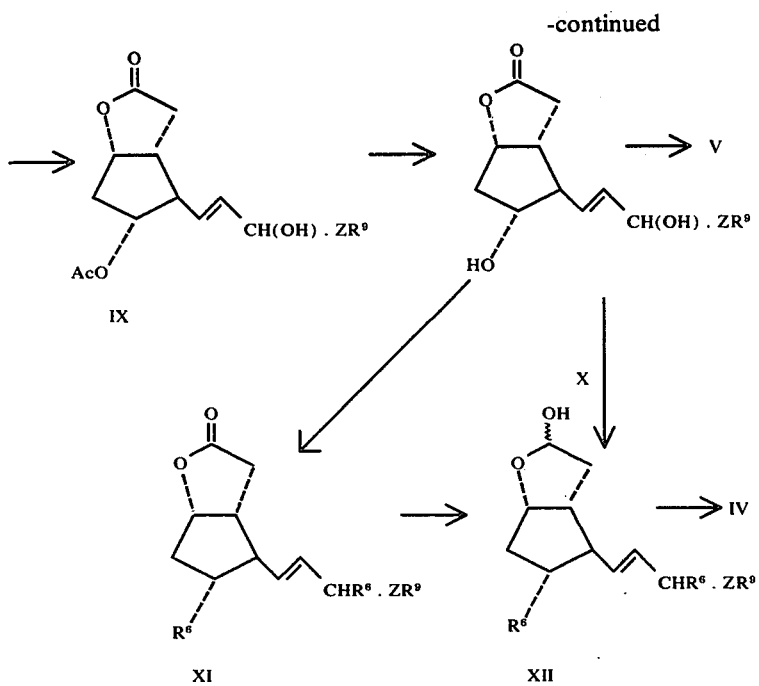

Ac represents an acetyl or p-phenylbenzoyl radical.

The starting material of the formula IV wherein X is an ethylene radical, used in the process of the invention, may be obtained by selective hydrogenation of the corresponding compound of the formula IV wherein X is the cis-vinylene radical, and the starting material of the formula IV wherein Y is the ethylene radical may be obtained by hydrogenation of an intermediate X or XI, and using the hydrogenation product in plce of the intermediate X or XI in the remainder of the above-described reaction sequence.

The starting material of the formula IV wherein $R^2$ is an alkanoyloxy radical may be obtained from the corresponding compound wherein $R^2$ is a hydroxy radical by acylation with an acid anhydride in pyridine to give a 9-ester-1-anhydride.

The starting material of the formula IV wherein $R^2$ and $R^3$ together form the oxo radical, may be obtained from the corresponding starting material of the formula IV wherein $R^2$ is hydroxy and $R^3$ is hydrogen, by oxidation aluminium trialkoxide, for example aluminium with Jones' reagent (chromic acid in acetone), followed, as required, by hydrolysis of the tetrahydropyranyl protecting groups or esterification of the carboxylic acid group.

The starting material of the formula V may be obtained by acid hydrolysis of the corresponding bis(tetrahydropyranyl ether) XII, ($R^6$ = tetrahydropyran-2-yloxy).

A starting material of the formula VI may be obtained from the known compound 4β-dimethoxymethyl-2,3,3aβ,6aβ-tetrahydro-5α-hydroxy-6β-iodo-2-oxocyclopenteno [b]furan (XIII) by treatment with tributyl tin hydride to give the de-iodinated lactone XIV. The 5α-hydroxy group is protected as the tetrahydropyran-2-yl ether XV, the lactone is reduced to the lactol XVI, using di-isobutyl aluminium hydride, and the lactol is reacted with (4-carboxy-butyl)-triphenyl-phosphonium bromide to give the cyclopentanol derivative XVII, which by reaction with toluene-p-sulphonic acid in methanol gives a methyl ester XVIII. The hydroxy groups are esterified, for example with 4-phenylbenzoyl chloride to give XIX, and the acetal is hydrolysed to an aldehyde XX which is reacted with a phosphonate $(CH_3O)_2PO.CH_2CO.ZR^9$ or a phosphorane $Ph_3P{:}CH.CO.ZR^9$ in the presence of a strong base, to give the required starting material of the formula VI, wherein X is cis-vinylene, and $R^7$ and $R^8$ are each an alkanoyloxy or aroyloxy radical.

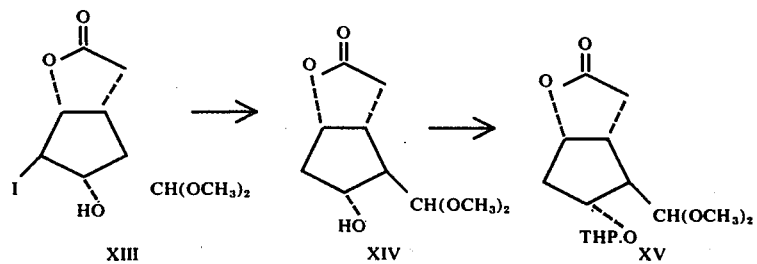

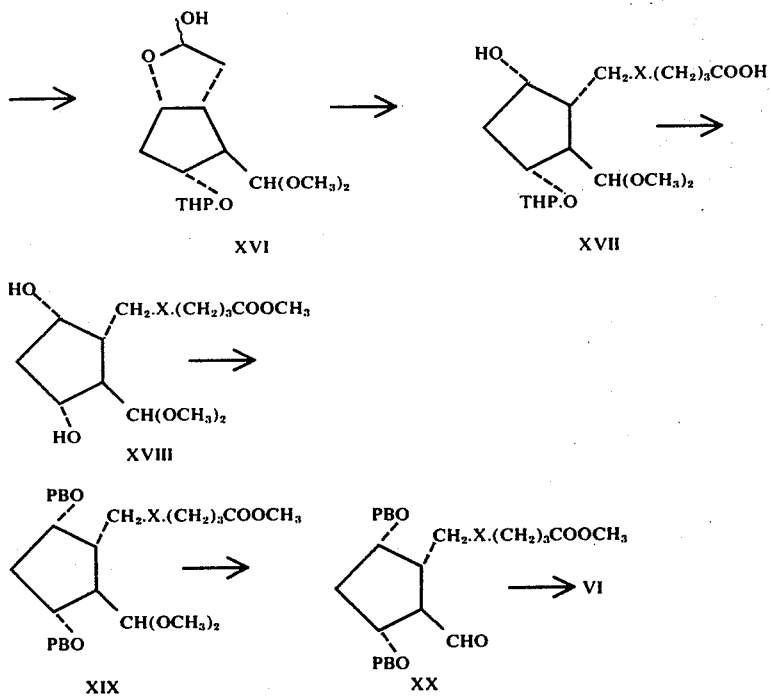

PB = phenylbenzoyl,
THP = tetrahydropyran-2-yl.

If a starting material of the formula VI wherein X is an ethylene radical is required, the methyl ester XVIII is hydrogenated, and the hydrogenated methyl ester is used instead of the methyl ester XVIII in the following steps of the process.

Alternatively, the cyclopentanol derivatives XVII is esterified with diazomethane to a methyl ester XXI, and the hydroxy radical is also esterified, for example with 4-phenylbenzoyl chloride, to give XXII. The tetrahydropyranyl ether group is hydrolysed with dilute acid in methanol, and the acetal XXIII is hydrolysed in a two phase system of concentrated hydrochloric acid in chloroform, to give a required starting material VI, wherein X is a cis-vinylene radical, $B^7$ is a 4-phenylbenzoyloxy radical and $B^8$ is a hydroxy radical.

either by resolving the corresponding racemate, or by carrying out the above-described reaction sequences starting from an optically active intermediate, for example from an optically active aldehyde of the formula VII(Ac = acetyl or p-phenylbenzoyl).

As stated above, the compounds of the invention possess a profile of pharmacological properties which differs from that of the naturally occuring prostaglandins $F_2\alpha$ and $E_2$. Thus, for example, 15-(5-chloro-2,3-dihydrobenzo[b] fur-2-yl)-9α,11α,15-trihydroxy-16,17,18,19,20-pentanor-5-cis, 13-trans-prostadienoic acid and 9α,11α,15-trihydroxy-15-(5-chloro-2-indanyl)-16,17,18,19,20-pentanor-5-cis,13-trans-prostadienoic acid are each approximately 50 times as active as prostaglandin $F_2\alpha$ in a luteolytic test in the

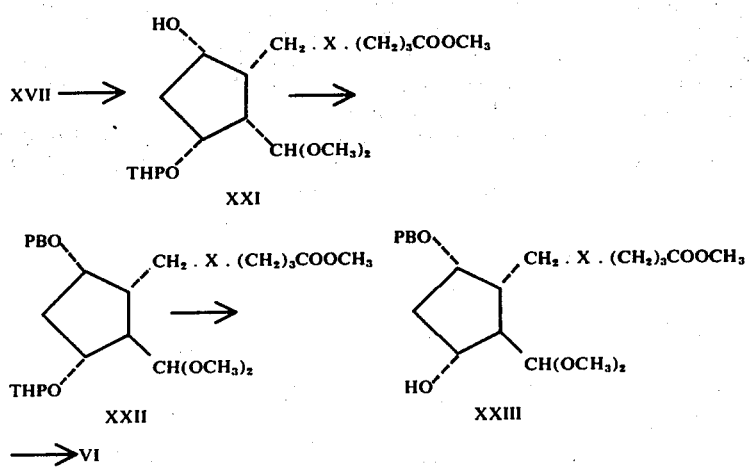

It is, of course, to be understood that an optically active compound of the invention may be obtained hamster (oral dosing), but have only about one fifth of the smooth muscle stimulant activity of prostaglandin F₂α. No indication of toxicity has been noted with any compound of the invention at the dose levels used.

Also as stated above, the compounds of the invention are useful, for example, for the induction of labour in childbirth, and for this purpose are used in the same way as it is known to use the naturally-occurring prostaglandins $E_1$ and $E_2$, that is to say, by administering a sterile, substantially aqueous solution containing from 0.01 to 10μg./ml., preferably 0.01 to 1μg./ml. of active compound, by intravenous, extraovular or intro-amniotic administration until labour commences. Also, for this purpose, the compounds of the invention may be used in combination or concurrently, with a uterine stimulant, for example oxytocin, in the same way that it is know to use prostaglandin $F_2α$ in combination, or concurrently with oxytocin for the induction of labour.

When a compound of the invention is to be used for the controi of the oestrus cycle in animals, it may be used in combination, or concurrently, with a gonadotrophin, for example PMSG (pregnant mare serum gonadotrophin) or HCG (human chorionic gonadotrophin) to hasten the onset of the next cycle.

Thus, according to a further feature of the invention there is provided a pharmaceutical or veterinary composition comprising a cyclopentane derivative of the invention, together with a pharmaceutically or veterinarily acceptable diluent or carrier.

The compositions may be in a form suitable for oral administration, for example tablets or capsules, in a form suitable for inhalation, for example an aerosol or a solution suitable for spraying, in a form suitable for parenteral or infusion administration, for example sterile injectable aqueous or oily solutions or suspensions, or in the form of a suppository, suitable for anal or vaginal use.

The compositions of the invention may be prepared by conventional means, and may incorporate conventional excipients, and a preferred composition is a sterile, substantially aqueous solution containing between 0.01 and 10.0μg./ml. of a compound of the invention.

The invention is illustrated, but not limited, by the following Examples. $R_F$ values refer to thin layer chromatography on silica gel plates supplied commercially by Merck of Darmstadt, and the spots were detected either by fluorescence, or by spraying the plates with a solution of ceric ammonium nitrate in sulphuric acid. Mass spectrum data for F-series compounds refer to the per(trimethylsilyl) derivatives, that is, normally, tetra-trimethylsilyl derivatives of compounds wherein $R^1$ is carboxy or hydroxymethyl, and tris-trimethylsilyl derivatives of compounds wherein $R^1$ is an alkoxycarbonyl radical. Mass spectrum data for E-series compounds refer normally to the tris-trimethylsilyl-9-methoxime derivatives.

EXAMPLE 1

A solution of 9α-hydroxy-15-(2,3-dihydrobenzo[b]fur-2-yl)-11α,15-bis-(tetra-hydropyran-2-yloxy)-16,17,18,19,20-pentanor-5-cis,13-trans-prostadienoic acid (193mg.) in 3ml. of a 2:1 mixture of acetic acid and water, was stirred at 50° C. for 2 hours. The solvents were evaporated, the residue was dissolved in dilute aqueous sodium bicarbonate solution (2ml.) and the solution was extracted with ethyl acetate (3 × 2ml.) and the extracts were discarded. The aqueous solution was acidified to pH 4 with 2N aqueous oxalic acid and the acidified solution was extracted with ethyl acetate (4 × 5ml.). The ethyl acetate extracts were washed with a 1:1 mixture of saturated brine and water, and were then dried. After evaporation of the ethyl acetate, the residue consisted of a mixture of the C-15 epimers of 9α,11α,15-trihydroxy-15-(2,3-dihydrobenzo[b]fur-2-yl)-16,17,18,19,20-pentanor-5-cis,13-trans-prostadienoic acid. Thin-layer chromatography on silica gel plates, supplied commercially by Merck of Darmstadt, using a mixture of 3% acetic acid in ethyl acetate as the developing solvent, separated the C-15 epimers, having $R_F$ values of 0.3 and 0.4, respectively. The n.m.r. spectrum of each isomer (in deuterated acetone) showed the following characteristic bands (δ values):

3.12, 2H, doublet, benzofuryl C-3 protons,
3.7–5.0, 7H, multiplet, 3-C$\underline{H}$(O$\underline{H}$)—and benzofuryl C-2 protons,
5.2–5.8, 4H, multiplet, olefinic protons,
6.6–7.2, 4H, multiplet, aromatic protons. The mass spectrum of the more polar epimer had M⁺ = 675.3365 (calculated for $C_{35}H_{62}O_6SI_4$ = 675.3391).

The bis-tetrahydropyranyl ether used as starting material may be prepared as follows:

n-Butyl-lithium (33ml. of a 2.1M solution in hexane) was added to a solution of dimethyl methylphosphonate (8.5g.) in dry tetrahydrofuran at −78° C. in an atmosphere of nitrogen. After 10 minutes, a solution of methyl 2,3-dihydrobenzo[b]furan-2-carboxylate (6.09g.) in dry tetrahydrofuran (35ml.) was added dropwise, and the mixture was stirred for 4 hours at −78° C. The reaction mixture was neutralised with acetic acid and the solvents were removed under reduced pressure. The residue was shaken with a mixture of ether (100ml.) and water (20ml.), and the organic phase was separated and washed with brine. The solution was dried, the solvents were evaporated and the residue was used without purification. $R_F$ = 0.5 (10% methanol in ethyl acetate).

A solution of dimethyl 2-oxo-2-(2,3-dihydrobenzo[b]-fur-2-yl)ethyl phosphonate (1.05g.) in dry 1,2-dimethoxyethane (20ml.) at −78° C. was treated with n-butyl-lithium (1.57ml. of a 2.1M solution in hexane), and the mixture was stirred for 15 minutes. To this mixture was added a solution of 5α-(4-phenylbenzoyloxy)-4β-formyl-2-oxo-2,3,3aβ, 6aβ-tetrahydrocyclopenteno[b]furan (1.05g.) in 1,2-dimethoxyethane (20ml.), and after 1 hour the reaction mixture was neutralised with glacial acetic acid and all solvents were removed by evaporation under reduced pressure below 35° C. The residue was triturated with ether to yield the unsaturated ketone product as a white solid, $R_F$ = 0.7 (1:1 ethyl acetate/toluene). The n.m.r. spectrum in deuteriochloroform showed the following characteristic features (δ values):

5.0–5.4, 3H, multiplet, C-5,C-6a and benzofuryl C-2 protons,
6.5–7.3, 6H, multiplet, olefinic and benzofuryl aromatic protons,
7.4–8.2, 9H, multiplet, other aromatic protons.

To a solution of the unsaturated ketone (566mg.) in toluene (25ml.) was added a solution of diisobornyloxyaluminium isopropoxide (8.9ml. of a 6.32M solution in toluene). After 10 minutes at room temperature saturated sodium hydrogen tartrate solution was added and the mixture was stirred for 10 minutes. Ethyl acetate (50ml.) was added, the organic phase was separated and dried, and the solvent was evaporated under reduced pressure to yield a mixture of epimeric enols $R_F$ = 0.4 and 0.5 (25% methylenedichloride in ethylacetate), contaminated with iso-borneol.

To a solution of the crude enol mixture (563mg.) in a mixture of methanol and methylene dichloride (4:1) was added anhydrous potassium carbonate (175mg.). After stirring for 3 hours at room temperature, the mixture was acidified to pH 5 with hydrochloric acid, and diluted with ethyl acetate (50ml.). This mixture was washed successively with saturated sodium bicarbonate solution and brine. The organic phase was separated and dried, and the solvents evaporated under reduced pressure. The crude product was chromatographed on "Florisil" (trademark) using ether as eluent, to yield an epimeric mixture of diols, $R_F = 0.3$ (5% methanol in methylene dichloride. The n.m.r. spectrum in deuteriochloroform showed the following features ($\delta$ values):

3.7–5.0, 4H, multiplet, C-5, C-6a, C-15 and benzofuryl C-2 protons, 5.63, 2H, multiplet, olefinic protons, 6.6-7.3, 4H, multiplet, aromatic protons.

To a solution of the epimeric diols (244mg.) in methylene chloride (2.5ml.) under an atmosphere of nitrogen were added successively redistilled 2,3-dihydropyran (0.7ml.) and a solution of anhydrous toluene-p-sulphonic acid in tetrahydrofuran (0.1ml. of a 1% solution).

After 10 minutes, pyridine (3 drops) was added, followed by ethyl acetate (40ml.). The solution was washed successively with saturated sodium bicarbonate solution and saturated brine, and was dried. Evaporation of the solvents gave a mixture of epimeric bis-tetrahydropyranyl ethers as a clear oil, $R_F = 0.6$ (ethyl acetate).

To a solution of the epimeric bis-tetrahydropyranyl ethers (390mg.) in dry toluene (20ml.) under an atmosphere of nitrogen at −78° C. was added 1.44ml. of a 2.2m mole/ml. solution of di-isobutylaluminium hydride in toluene. After 15 minutes the reaction was quenched by the dropwise addition of methanol (3ml.) and after a further 15 minutes at room temperature a mixture of 1:1 saturated brine/water (25ml.) was added, and the mixture was extracted with ethyl acetate (3 × 50ml.). The extract was washed with saturated brine, and dried, and the solvents were evaporated to give a mixture of epimers of the bis-(tetrahydropyranyl ether) lactol, 4$\beta$-[4-(2,3-dihydrobenzo[b]fur-2-yl)-3-(tetrahydropyran-2-yloxy)-1-trans-butenyl]-2,3,3a$\beta$,6a$\beta$-tetrahydro-2-hydroxy-5$\alpha$-(tetrahydropyran-2-yloxy)cyclopenteno[b]furan, $R_F = 0.5$ (5% methanol in methylene dichloride).

Finely powdered (4-carboxybutyl)triphenylphosphonium bromide (886mg.) was heated to 100° C. under vacuum for 1 hour. The evacuated reaction vessel was filled with an atmosphere of dry nitrogen, the solid was dissolved in dimethylsulphoxide (5ml.) and the solution was cooled to room temperature. To this solution was added dropwise 1.93 ml. of a 2M solution of methanesulphinylmethyl sodium in dimethylsulphoxide followed by a solution of the mixture of epimers of the bis-(tetrahydropyranyl ether) lactol (373 mg.) in a mixture of dimethylsulphoxide (10ml.) and benzene (2ml.). The solution was stirred for 3 hours, and the solvent was removed by evaporation under reduced pressure at a temperature below 40° C. The residue was shaken with water (10ml.) and ethyl acetate (10ml.) and the aqueous phase was separated, extracted with ethyl acetate (2 × 10ml.) and the extracts discarded. The aqueous solution was acidified to pH 3–4 with 2N aqueous oxalic acid, and extracted with a mixture of equal parts of ether and petroleum ether (b.p. 40°–60° C.) (5 × 10ml.). The organic phase was separated, washed with saturated brine and was dried. Evaporation of the solvents gave 15-(2,3-dihydrobenzo[b]fur-2-yl)-9$\alpha$-hydroxy-11$\alpha$,15-bis-(tetrahydropyran-2-yloxy)-16,17,18,19,20-pentanor-5-cis, 13-trans-prostadienoic acid as a clear oil, $R_F = 0.3$, (5% methanol in methylene dichloride.

EXAMPLE 2

Methyl 15-(benzo[1,4]dioxan-2-yl)-15-oxo-9$\alpha$,11$\alpha$-di-(4-phenylbenzoyloxy)-16,17,18,19,20-pentanor-5-cis,13-trans-prostadienoate (185mg.) was stirred in dry toluene (4.0ml.) under argon at room temperature, and treated with a 0.323M solution of di-isobornyloxyaluminium isopropoxide in toluene (2.17ml., 3 equivalents). After 1¼ hours, the mixture was partitioned between water (0.5ml.) and ethyl acetate (1.0ml.), and filtered through 'Hyflo' (trademark) washing the filter pad with ethyl acetate (2 × 4ml.). The organic layer was separated, washed with brine (4ml.), dried over magnesium sulphate and filtered, and the solvent was evaporated to leave a crude oily product, which was chromatographed on 'Florisil' (2g.). Elution with 5–10% ethyl acetate in toluene gave the enol, methyl 15-(benzo-[1,4]dioxan-2-yl)-15-hydroxy-9$\alpha$,11$\alpha$-di-(4-phenylbenzoyloxy)-16,17,18,19,20-pentanor-5-cis,13-trans-prostadienoate, $R_F = 0.4$ (25% ethyl acetate in toluene).

The enol (64mg.) was stirred at room temperature under argon in a mixture of methanol (0.8ml.), water (0.6ml.) and acetone (1.0ml.) with potassium hydroxide (0.8ml. of a 1M solution in methanol), for 16 hours. The solvents were evaporated under reduced pressure and the residue was partitioned between water (12ml.) and ether (3 × 10ml.). The aqueous layer was separated and filtered through 'Hyflo' washing the filter pad with water (2ml.). The filtrate was acidified to pH 1 with 2N hydrochloric acid and extracted with ether (3 × 10ml.). The combined ether extracts were washed in brine (5ml.), dried over magnesium sulphate and filtered, and the solvent was evaporated to leave a solid residue consisting of 4-phenylbenzoic acid and a mixture of the C-15 epimers of 15-(benzo[1,4]dioxan-2-yl)-9$\alpha$,11$\alpha$,15-trihydroxy-16,17,18,19,20-pentanor-5-cis,13-trans-prostadienoic acid. The epimers were separated by preparative thin layer chromatography on silica gel, $R_F = 0.3$ and 0.4 (5% acetic acid in ethyl acetate). The n.m.r. spectrum of each epimer in deuteriochloroform showed the following characteristic features ($\delta$ values):

3.8–4.3, 6H, multiplet, 3>C$\underline{H}$(OH) and C-2 and C-3 protons of the benzodioxanyl radical, 4.8, 3H, broad, 3 hydroxy protons, 5.1–5.8, 4H, multiplet, olefinic protons, 6.88, 4H, singlet, aromatic protons.

The mass spectrum of the more polar epimer had $M^+ = 706.3562$ (calculated for $C_{35}H_{62}O_7Si_4 = 706.3574$).

The methyl 15-(benzo[,4]dioxan-2-yl)-15-oxo-9$\alpha$,11$\alpha$-di-(4-phenylbenzoyloxy)-16,17,18,19,20-pentanor-5-cis,13-trans-prostadienoate used as starting material may be prepared as follows:

Methyl benzo [1,4]dioxan-2-carboxylate was converted to dimethyl [2-(benzo[1,4]dioxan-2-yl)-2-oxo]ethylphosphonate by the process described in the second part of Example 1, b.p. 234° C. at 0.1mm/Hg, $R_F = 0.3$ (50% ethyl acetate in toluene).

A solution of dimethyl [2-(benzo[1,4]dioxan-2-yl)-2-oxo]ethylphosphonate (131mg.) (1.5 equivalent) in dimethoxyethane (2.0ml.) was stirred under argon and cooled in a chloroform 'Drikold' bath, and treated with 2.2M butyllithium in hexane (177 μl.) followed after a few minutes by a solution of methyl 7-[2β-formyl-3α,-5α-di(4-phenylbenzoyloxy)-cyclopent-1α-vl]hept-5-cis-enoate (225.7mg.), also in dimethoxyethane (1.5ml.). The cooling bath was then removed, and after 2 hours a few drops of acetic acid and then water (200μl.) were added to adjust the pH to about 6. The solvent was evaporated under reduced pressure and the residue was partitioned between water (15ml.) and ethyl acetate (1 × 30ml., 1 × 15). The organic layer was separated, washed with water (10ml.) then dried over magnesium sulphate, and filtered, and the solvent was evaporated to give a viscous oil. This oil was purified either by chromatography on 'Florisil' (2g.) eluting with 5% ethyl acetate in toluene or by trituration with methanol (10ml.), to afford the enone, methyl 15-(benzo[1,4]dioxan-2-yl)-15-oxo-9α,11α-di-(4-phenylbenzoyloxy)-16,17,18,19,20-pentanor-5-cis, 13-trans-prostadienoate, $R_F = 0.7$ (ether).

The aldehyde, methyl 7-[2β-formyl-3α,5α-di(4-phenylbenzoyloxy)cyclopent-1α-yl]hept-5-cis-enoate, used in the above process, may be prepared as follows:

4β-Dimethoxymethyl-2,3,3aβ,6aβ-tetrahydro-5α-hydroxy-6β-iodo-2-oxocyclopenteno[b]furan (4.0g.) in dry toluene (40ml.) was stirred under argon at 80° C. with tri-n-butyl tin hydride (6.6g.) for 18 hours. The solvent was evaporated under reduced pressure and the residue was stirred with petroleum ether (b.p. 40°-60° C., 100ml.) for 30 minutes. The solvent was decanted and the residual oil was chromatographed on "Florisil" (trade mark) (50g.). Elution with mixtures containing 25% ethyl acetate in toluene and finally with ethyl acetate gave 4β-dimethoxymethy-2,3,3aβ,6aβ-tetrahydro-5α-hydroxy-2-oxocyclopenteno[b]furan as an oil, $R_F$ = 0.3 (20% acetone in chloroform). The n.m.r. spectrum in deuteriochloroform showed the following characteristic peaks (δ values):

| 3.40 and 3.42, 6H, 2 singlets, methoxy |
|---|
| 4.04–4.36    1H, multiplet, 5β proton, |
|                1H, doublet, —CH(OMe)₂, |
|                1H, multiplet, 6aβ proton. |

4β-Dimethoxymethyl-2,3,3aβ,6aβ-tetrahydro-5α-hydroxy-2-oxocyclopento[b]furan (4.01g.) was stirred under argon in dry toluene (30ml.), and the resulting solution was treated with an excess of freshly distilled 2,3-dihydropyran (17ml.), followed by 2.0ml. of a 0.1% w/v solution of toluene-p-sulphonic acid in dry tetrahydrofuran. After ¾ hour, the mixture was treated with pyridine (0.50ml.) and then partitioned between ethyl acetate (150ml.) and saturated sodium bicarbonate (75ml.). The organic layer was separated, washed with saturated brine (50ml.), dried over magnesium sulphate and filtered, and the solvent was evaporated to give a crude lactone, 4β-dimethoxymethyl-2,3,3aβ,6aβ-tetrahydro-2-oxo-5α-(tetrahydropyran-2-yloxy)-cyclopenteno[b]furan, $R_F$ = 0.70 (20% acetone in chloroform). The crude lactone (6.2g.) was dissolved by stirring in dry 1,2-dimethoxyethane (120ml.) under argon at about −60° C. (chloroform — 'Drikold' (trademark) cooling bath), and 1.7M diisobutylaluminium hydride (11.2ml.) was added. After 30 minutes, methanol (3ml.) was added, the mixture was allowed to warm up to room temperature, and was partitioned between ethyl acetate (600ml.) and 1:1 saturated brine/water (300ml.). The whole mixture was filtered through keiselguhr ("Hvflo" — trade mark) and the two phases were separated. The aqueous phase was reextracted with ethyl acetate (300ml.) and the combined organic layers were washed with water (100ml.), dried over magnesium sulphate and filtered, and the solvents were evaporated to give the crude lactol, 4β-dimethoxymethyl-2,3,3aβ,6aβ-tetrahydro-2-hydroxy-5α-(tetrahydropyran-2-yloxy)-cyclopenteno[b]furan, as an oil, $R_F$ = 0.4 (20% acetone in chloroform).

A stirred solution of (4-carboxybutyl)triphenylphosphonium bromide (24.8g.) in dry dimethylsulphoxide (DMSO, 50ml.), was treated slowly under argon and with cooling in an ice-water bath, with 2M methanesulphinylmethyl sodium in DMSO (54.5ml., 2.5 equivalents) to form a solution of the corresponding ylide. The crude lactol (6.3g.) in dry DMSO (150ml.) was then added to the ylide solution at room temperature. The mixture was stirred for 1¼ hours, then water (1ml.) was added. The DMSO was then evaporated at high vacuum at a temperature not exceeding 50° C. The residual gum was partitioned between ether (4 × 225ml.) and water (150ml.). The aqueous layer was separated, acidified with 2N oxalic acid to approximately pH 4, and then extracted with 1:1 mixture of ether and pentane (3 × 300ml.). The extracts were washed with saturated brine (150ml.), dried over magnesium sulphate and filtered, and the solvent was evaporated to give the crude acid, 7-[2β-dimethoxymethyl-5α-hydroxy-3α-(tetrahydropyran-2-yloxy)-cyclopent-1α-vl]hept-5-cis-enoic acid as an oil, suitable for use in the next stage of the synthesis. A sample was purified by chromatography on silica (70:1) eluting the product was 2% methanol in toluene as an oil, $R_F$ = 0.4 (5% methanol in methylene chloride). The n.m.r. spectrum in deuteriochloroform showed the following characteristic peaks (δ values):

| 3.35, 6H, singlet, methoxy, |
|---|
| 3.3–3.65, 1H, |
| 3.68–4.0, 1H, |
| 4.00–4.19, 2H,      multiplets, >CH—O— |
| 4.19–4.38, 1H, |
| 4.6–4.8, 1H, |
| 5.09–5.78, 2H, multiplet, olefinic protons |

The crude acid (4.48g.) in methanol (45ml.) was stirred under argon at room temperature with toluene-p-sulphonic acid (240mg.) for 2¾ hours. The solution was then partitioned between ethyl acetate (300ml.) and saturated sodium bicarbonate (60ml.) followed by saturated brine (60ml.). The organic phase was dried over magnesium sulphate and filtered, and the solvent was evaporated to leave a crude ester-diol, methyl 7-[2β-dimethoxymethyl-3α,5α-dihydroxycyclopent-1α-yl]hept-5-cis-enoate as an oil, $R_F$ = 0.65 (10% methanol in methylene chloride). The n.m.r. spectrum in deuteriochloroform showed the following principal peaks (δ values):

| | |
|---|---|
| 3.39, 6H, singlet, | 3 methyl groups, |
| 3.64, 3H, singlet, | |
| 4.03–4.3, 3H, | multiplet, >C$\underline{H}$—O— |
| | doublet, >C$\underline{H}$(OMe)$_2$ |
| 5.1–5.7, 2H, multiplet, olefinic protons. | |

The crude ester-diol (3.3g) was dissolved in dry pyridine (50ml.) under argon, and treated with p-phenylbenzoyl chloride (9.2g.), and the mixture was stirred for 17 hours. Water (0.8ml.) was then introduced and stirring was continued for 3–4 hours. The mixture was evaporated under reduced pressure and toluene was added to assist azeotropic removal of the pyridine. The residue was partitioned between toluene (300ml.) and saturated sodium bicarbonate solution (150ml.). The whole mixture was filtered through 'Hyflo' and the organic phase was separated. The aqueous layer was extracted with toluene (150ml.), and the organic extracts were combined, washed with brine (100ml.), dried over magnesium sulphate, and filtered, and the solvent was evaporated to leave a solid crystalline residue. This was thoroughly triturated with methanol (70ml.), the mixture was filtered, and the product was washed with more methanol (3 × 10ml.) to give the dimethyl acetal, methyl 7-[2β-dimethoxymethyl-3α,-5α-di-(4-phenylbenzoyloxy)cyclopent-1α-vl]hept-5-cis-enoate as a white solid, m.p. 104.5–106.5° C., R$_F$ = 0.5 (5% acetone in toluene). The n.m.r. spectrum in deuteriochloroform showed the following characteristic signals (δ values):

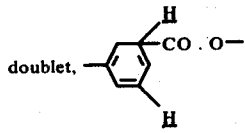

| | |
|---|---|
| 3.41, 3H, singlet | |
| 3.47, 3H, singlet | methyls, |
| 3.52, 3H, singlet | |
| 4.59–4.61, 1H, | doublet, >C$\underline{H}$(OMe)$_2$, |
| 5.17–5.70, 4H, | multiplet, 2 × >C$\underline{H}$—O— and 2 olefinic protons, |
| 7.80–8.00, 2H, | doublet, |
| 8.00–8.20, 2H, | |

An analytical sample recrystallised three times from ethanol had m.p. 105°–107° C. The dimethyl acetal was vigorously stirred under argon for 10 minutes in a two-phase system consisting of 2% isopropanol in chloroform (20ml.) and concentrated hydrochloric acid (10ml.). The chloroform layer was separated and the aqueous layer was extracted with chloroform (20ml.). The organic layers were combined, washed successively with aqueous saturated sodium bicarbonate (20ml.) and saturated brine (10ml.), dried over magnesium sulphate and filtered, and the solvent was evaporated. The oily residue crystallised on drying under high vacuum to give methyl 7-[2β-formyl-3α,5α-di-(4-phenylbenzoyloxy)-cyclopent-1α-yl]hept-5-cis-enoate, R$_F$ = 0.4 (5% ethyl acetate in toluene). The n.m.r. spectrum in deuteriochloroform was consistent with the required structure, and showed the following principal signals (δ values):

| | |
|---|---|
| 3.51, 3H, singlet, methyl ester, | |
| 5.3–5.6, 4H, multiplet, >C$\underline{H}$—O— and olefinic protons, | |
| 7.8–8.0, 2H, | doublets, |
| 8.0–8.2, 2H, | |
| 7.22–7.73, 14H, multiplet, rest of aromatic protons, | |
| 10.01–10.14, 1H, doublet, —C$\underline{H}$O. | |

An analytical sample, m.p. 93°–97° C., was obtained by triturating the above-described product with ether.

EXAMPLE 3

The process described in Example 1 was repeated using 9α-hydroxy-15-(2-indanyl)-11α,15-bis-(tetrahydropyran-2-yloxy)-16,17,18,19,20-pentanor-5-cis-13-trans-prostadienoic acid in place of the corresponding benzofuryl compound, to give 9α,11α,15-trihydroxy-15-(2-indanyl)-16,17,18,19,20-pentanor-5-cis,13-trans-prostadienoic acid, R$_F$ = 0.4 and 0.5. (3% acetic acid in ethyl acetate). The n.m.r. spectrum of each epimer in deuteriochloroform showed the following characteristic peaks (δ values):

2.85, 4H, doublet, indanyl C-1 and C-3 protons,
3.2–4.1, 8H, multiplet, 3>C$\underline{H}$.O—, 4 exchangeable protons and indanyl C-2 proton,
7.0–7.2, 4H, multiplet, aromatic protons;

The mass spectrum of the more polar isomer had M$^+$ = 688.3827, (calculated for C$_{36}$H$_{64}$O$_5$Si$_4$ = 688.3832) prepared via the following intermediates: dimethyl [2-(2-indanyl)-2-oxolethylphosphonate, b.p. 85° C. at 0.1 mm. Hg.; unsaturated ketone, R$_F$ = 0.6 (50% ethyl acetate in toluene). Mass spectrum gave (M-4-phenylbenzoic acid)$^+$ = 294.1227, calculated for C$_{19}$H$_{18}$O$_3$ = 294.1255;

enol R$_F$ = 0.3 and 0.25 (50% ethyl acetate in toluene); diol, R$_F$ = 0.4 (ethyl acetate);
bis-(tetrahydropyranyl ether) R$_F$ = 0.7 (ethyl acetate);
bis-(tetrahydropyranol ether) lactol, R$_F$ = 0.6 (ethyl acetate);
9α-hydroxy-15-(2-indanyl)-11α,15-bis-(tetrahydropyran-2-yloxy)-16,17,18,19,20-pentanor-5-cis, 13-transprostadienoic acid, R$_F$ = 0.4 (ethyl acetate)

EXAMPLE 4

The process described in Example 1 was repeated, using the appropriate phosphonate reagent, to give the compounds shown below. The products were identified by n.m.r. spectroscopy and are characterised below by accurate mass measurement by mass spectrometry of the molecular ion of the tetra(trimethylsilyl) derivative. The phosphonate reagent and the unsaturated ketone intermediate of the formula VIII, (Ac = p-phenylbenzoyl) have been characterised, and appropriate data for these compounds are also given.

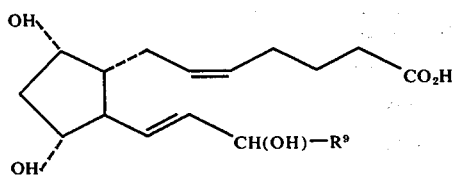

accurate mass measurement by mass spectrometry of the molecular ion or the (M - methyl)$^+$ ion, whichever is more appropriate, of the tetra (trimethylsily) derivative. The phosphonate reagent and the unsaturated ketone intermediate of the formula VI have been characterised and appropriate data for these compounds are also given.

| No. | R$^9$ | Isomer* | Mass Spectrum Found | Calculated | Phosphonate R$_F$ | Enone of formula VIII Ac = p-phenylbenzoyl |
|---|---|---|---|---|---|---|
| 1 | 5-chloro-2,3-dihydro-benzo[b]fur-2-yl | l.p. | 724 | | 0.38 | m.p. 161–163° C. |
| | | m.p. | M$^+$ = 724.3166 | 724.3235 | (ethyl acetate) | |
| 2 | 2-benzo[1,3]dioxolyl | l.p. | 692 | | 0.29 | R$_F$ = 0.6 |
| | | m.p. | M$^+$ = 692.3424 | 692.3417 | (50% ethyl acetate in methylene dichloride) | (50% ethyl acetate in toluene) |
| 3 | 1-benzocyclobutyl | mixed | M$^+$ = 674.3686 | 674.3676 | 0.35 (5% methanol in ethyl acetate) | R$_F$ = 0.45 (25% ethyl acetate in toluene) |

*l.p. = less polar isomer
m.p. = more polar isomer

EXAMPLE 5

The process described in Example 2 was repeated using the appropriate phosphonate reagent, to give the compounds shown below. The products were identified by n.m.r. spectroscopy and are characterised below by

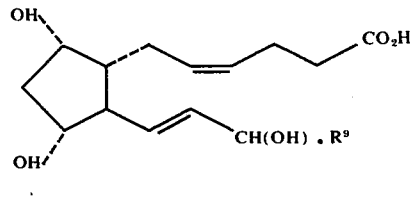

| No. | R$^9$ | Isomer* | Mass spectrum Found | Calculated | Phosphonate R$_F$ | Enone of the formula VI |
|---|---|---|---|---|---|---|
| 1. | 2-methylindan-2-yl | l.p. | 673 | | 0.5 | (M—Ph.C$_6$H$_4$CO$_2$)$^+$ = 588.2879 |
| | | m.p. | (M—CH$_3$—CH$_2$)$^+$= 673.3616 | 673.3598 | (a) | (Calculated = 588.2876) |
| 2. | 1-methylindan-2-yl | l.p. | 702 | | 0.4 | R$_F$ = 0.8 |
| | | m.p. | M$^+$ = 702.3963 | 702.3989 | (a) | (b) |
| 3. | 5-methylindan-2-yl | l.p. | 687 | | 0.2 | (M—PhC$_6$H$_4$CO$_2$)$^+$ = 588.2862 |
| | | m.p. | M$^+$—CH$_3$= 687.3700 | 687.3655 | (c) | (calculated = 588.2376) |
| 4. | 5-chloroindan-2-yl | l.p. | 722 | | 0.1 | (M—PhC$_6$H$_4$CO$_2$)$^+$ = 608.2264 |
| | | m.p. | M$^+$ = 722.3369 | 722.3442 | (c) | (Calculated = 608.2329) |
| 5. | 5,6-dichloroindan-2-yl | l.p. | 756 | | 0.15 | (M—PhC$_6$H$_4$CO$_2$)$^+$ = 642.1949 |
| | | m.p. | M$^+$ = 756.2997 | 756.3052 | (d) | (Calculated = 642.1938) |
| 6. | 1-indanyl | l.p. | 687 | | 0.5 | R$_F$ = 0.5 |
| | | m.p. | M$^+$—CH$_3$ = 573.3495 | 673.3598 | (e) | (b) |
| 7. | 2-indanylmethyl | mixed | M$^+$ = 702.3943 | 702.3989 | 0.2 (d) | (M—PhC$_6$H$_4$CO$_2$)$^+$ = 588.2903 (Calculated = 588.2876) |
| 8. | 2-(2-indanyl)ether | l.p. | 701 | | 0.2 | (M—PhC$_6$H$_4$CO$_2$)$^+$ = 602.3006 |
| | | m.p. | (M—CH$_3$)$^+$ = 701.3860 | 701.3910 | (d) | (Calculated = 602.3032) |
| 9. | 1,2,3,4-tetrahydro-2-naphthyl | mixed | M$^+$ = 702.3979 | 702.3989 | 0.1 (f) | R$_F$ = 0.75 (b) |
| 10. | 2,3-dihydro-5-methoxy-benzo[b]fur-2-yl | l.p. | 720 | | | R$_F$ = 0.5 |
| | | m.p. | M$^+$ = 720.3717 | 720.3731 | (k) | (g) |
| 11. | 2,3-dihydro-6-methoxy-benzo[b]fur-2-yl | l.p. | 720 | | | R$_F$ = 0.6 |
| | | m.p. | M$^+$ = 720.3696 | 720.3731 | (l) | (g) |
| 12. | 5-chloro-2-methyl-chroman-2-yl | l.p. | 752 | | 0.12 | R$_F$ = 0.69 |
| | | m.p. | M$^+$ = 752.3542 | 752.3546 | (f) | (g) |
| 13. | 3-methylbenzo[1,4]oxazin-2-yl | l.p. | 719 | | 0.1 | R$_F$ = 0.83 |
| | | m.p. | M$^+$ = | | | |

-continued

| No. | R⁹ | Isomer* | Mass spectrum Found | Calculated | Phosphonate R_F | Enone of the formula VI |
|---|---|---|---|---|---|---|
| 14. | benzo[b]fur-2-yl | mixed | 719.3895 M⁺ = | 719.3890 | (f) 0.45 | (f) |
| 15. | benzo[b]thien-2-yl | mixed | 688.3480 M⁺ = 704.3241 | 688.3468 704.3240 | (h) 0.44 (h) | (i) R_F = 0.86 (j) |
| 16. | benzo[b]thien-3-yl | l.p. m.p. | 704 M⁺ = 704.3242 | 704.3240 | 0.32 (h) | (m) |

*l.p. = less polar isomer
 m.p. = more polar isomer
(a) solvent system ; 10% methanol in methylene dichloride
(b) solvent system ; 25% ethyl acetate in toluene
(c) solvent system ; 10% ethyl acetate in methylene dichloride
(d) solvent system ; 25% ethyl acetate in methylene dichloride
(e) solvent system ; 10% methanol in ethyl acetate
(f) solvent system ; 50% ethyl acetate in toluene
(g) solvent system ; 20% ethyl acetate in toluene
(h) solvent system ; ethyl acetate
(i) In this example, the enone was prepared in the following manner:-
   A solution of methyl 7-[2β-formvl-3α,5α-di-(4-phenylbenzoyloxy)-cyclopent-1α-yl]hept-5-cis-enoate (200mg., 0.34 mmole) in dimethylformamide (2ml.) was added to a mixture of dimethyl 2-(benzo[b]furan-2-yl)-2-oxoethylphosphonate (136mg., 0.5 mmole) and sodium hydride (19mg., 0.45 mmole) in dimethylformamide (4ml.) at room temperature. After 1 hour the mixture was diluted with water (10ml.) and extracted with ethyl acetate (3 × 5ml.). The combined extracts were dried and the solvent was evaporated in vacuo to give the desired enone, $R_F = 0.35$ (50% ethyl acetate in pentane).
(j) solvent system ; 10% methanol in toluene
(k) characterised by its n.m.r. spectrum in deuteriochloroform (δ values):-

3.35 & 3.72, 2H, double doublet, $-C\underline{H}_2-P\big<$, 3.58, 2H, doublet, dihydrofuryl C-3 Protons, 3.81 & 4.00, 6H, double doublet, $\!\!>\!\!P-(O-C\underline{H}_3)_2$.

3.90, 3H, singlet, aromatic methoxy protons,
   5.29, 1H, triplet, dihydrofuryl C-2 proton,
   6.87, 3H, singlet, aromatic protons.
(l) Characterised by its n.m.r. spectrum in deuteriochloroform (δ values):-

3.20 & 3.59, 2H, double doublet, $-C\underline{H}_2-P\big<$, 3.36, 2H, doublet, dihydrofuryl C-3 protons, 3.68 & 3.87, 6H, double doublet, $\!\!>\!\!P-(OC\underline{H}_3)_2$, 3.75, 3H, singlet, aromatic methoxy protons,
   5.23, 1H, triplet, dihydrofuryl C-2 protons,
   6.3–7.2, 3H, multiplet, aromatic protons.
(m) In this example the enone was prepared in the following manner:-
   A solution of methyl 7-[2β-formyl-3α,5α-di-(4-phenylbenzoyloxy)evelopent-1α-yl]hept-5-cis-enoate (79mg., 0.12 mmole) and dimethyl 2-(benzo[b]thien-3-yl)-2-oxoethylphosphonate (71mg., 0.25 mmole) in toluene (2ml.) and t-butanol (1ml.) was treated with 1N sodium hydroxide solution (212μl.) and stirred vigorously overnight. The mixture was neutralised with hydrochloric acid, the organic phase was separated, and the aqueous layer was extracted with methylene dichloride (3 × 5ml.). The combined organic extracts were dried, and the solvent was evaporated in vacuo to give the desired enone, $R_F = 0.66$ (20% ethyl acetate in toluene).

2-Ethoxycarbonyl-4-methyl-1,4-benzoxazine, used as a starting material for the preparation of compound number 13, was prepared as follows:

Ethyl 1,4-benzoxazine-2-carboxylate (5.8g.) was dissolved in acetonitrile (15ml.) under an atmosphere of argon. Formaldehyde (30ml. of a 37% aqueous solution) and lithium cyanoborohydride (4.67g.) were added, and the solution was stirred for 5 minutes. Glacial acetic acid (3.5ml.) was added dropwise and over a period of 10 minutes, and the solution was stirred at room temperature for 2 hours. More glacial acetic acid (3.5ml.) was added, and after 30 minutes the reaction mixture was poured into diethyl ether (200ml.), washed successively with 0.1N hydrochloric acid, sodium bicarbonate and brine, and was dried. The solvent was evaporated to give the crude 2-carboxyethyl-4-methyl-1,4-benzoxazine, which was purified by chromatography on silica gel (148g.). Elution with 10% ethyl acetate in toluene gave pure ethyl 4-methyl-1,4-benzoxazine-2-carboxylate (5.9g.) whose n.m.r. spectrum in deuteriochloroform showed the following features (δ values):

1.3, 3H, triplet (J = 7Hz), —CH₂C<u>H</u>₃,
2.9, 3H, singlet, N-M<u>e</u>,
3.45, 2H, doublet (J = 4Hz), >N-C<u>H</u>₂—CH<,
4.3, 2H, quartet, (J = 7Hz), —C<u>H</u>₂—CH₃,
4.9, 1H, triplet, (J = 4Hz), —CH₂C<u>H</u><,
6.6–7.0, 4H, multiplet, aromatic protons.

EXAMPLE 6

A solution of 15-(5-chloro-2,3-dihydrobenzo[b]fur-2yl)-9-oxo-11α,15-bis(tetrahydropyran-2-yloxy)-16,17,18,19,20-pentanor-5-cis,13-trans-prostadienoic acid (68mg.) in tetrahydrofuran (0.5ml.) and a 2:1 mixture of acetic acid and water (4ml.) was stirred at 50° C. for 1 hour. The solvents where then evaporated in vacuo and the residue was chromatographed on a column of Mallinkrodt CC4 silica gel (4.4g.) using 30% acetone in cyclohexane as eluant. Evaporation of the solvent gave the mixture of C-15 epimers of 15-(5-chloro-2,3-dihydrobenzo[b]fur-2-yl)-11α,15-dihydroxy-9-oxo-16,17,18,19,20-pentanor-5-cis,13-trans-prostadienoic acid, $R_F$ = 0.3 and 0.4 respectively (3% acetic acid in ethyl acetate). The n.m.r. spectrum in deuterated acetone showed the following characteristic features (δ values):

3.17, 2H, doublet, dihydrofuryl C-3 proton,
3.9–4.4, 2H, multiplet, 2 -C<u>H</u>(OH)—,
4.78, 1H, multiplet, dihydrofuryl C-2 proton,
5.34, 2H, multiplet, cis-olefinic protons,
5.78, 2H, multiplet, trans-olefinic protons,
6.6-7.2, 3H, multiplet, aromatic protons.

The mass spectrum showed M⁺ = 679.2902 (calculated for $C_{33}H_{54}ClNO_6Si_3$ = 679.2947).

The starting material for the above process was obtained as follows:

A solution of 15-(5-chloro-2,3-dihydrobenzo[b]-fur-2-yl)-9α-hydroxy-11α,15-bis(tetrahydropyran-2-vloxy)-16,17,18,19,20-pentanor-5-cis,13-trans-prostadienoic acid (96mg. 0.16 mmole) in acetone (2ml.) at 0° C., was treated with 8N chromic acid (51.74μl., 0.41 mmole) for 45 minutes. Isopropanol was added, and the solution was diluted with ethyl acetate (15ml.), washed with brine (10ml.) and dried. Evaporation of the solvent gave the mixed C-15 epimers of 15-(5-chloro-2,3-dihydrobenzo[b]fur-2-yl)-9-oxo-11α,15-bis(tetrahydropyran-2-vloxy)-16,17,18,19,20-pentanor-5-cis,13-trans-prostadienoic acid, $R_F$ = 0.4 (5% methanol in methylene dichloride).

This bis(tetrahydropyranyl) ether used in the preparation was obtained by the process described in the second part of Example 1, using methyl 5-chloro-2,3-dihydrobenzo[b]furan-2-carboxylate in place of methyl 2,3-dihydrobenzo[b]furan-2-carboxylate.

EXAMPLE 7

The process described in Example 6 was repeated, using the appropriate bis(tetrahydropyranyl) ether obtained as described in Example 1, to give the 9-oxo componds shown in the table below. The products were identified by n.m.r. spectroscopy and are characterised by accurate mass measurement by mass spectrometry of the molecular ion of the methoxime-tris(trimethylsilyl) derivative, or in the case of compound 4 the methoxime-bis(trimethylsilyl ether)-methyl ester derivative.

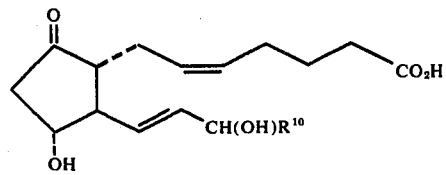

| No. | R | Isomer* | Mass spectrum Found | Calculated |
|---|---|---|---|---|
| 1. | 2,3-dihydrobenzo[b]fur-2-yl | mixed | M⁺ = 645.3338 | 645.3337 |
| 2. | benzo[1,3]dioxol-2-yl | mixed | M⁺ = 647.3129 | 647.3129 |
| 3. | 1-benzocyclobutanyl | mixed | M⁺ = 629.3376 | 629.3388 |
| 4 | 2-indanyl | l.p. | 585 | |
| | | m.p. | M⁺ = 585.3303 | 585.3306 |

*l.p. = less-polar isomer
m.p. = more-polar isomer

EXAMPLE 8

The process described in the first part of example 2 as repeated using methyl 15-(5-chloroindan-2-yl)-11α4-dihydroxy-2-methyl-9α-(4-phenylbenzoyloxy)-16,17,18,19,20-pentanor-5-cis,13-trans-prostadienoate as the starting material, to give 15-(5-chloroindan-2-yl)-9α,11α,15-trihydroxy-2-methyl-16,17,18,19,20-pentanor-5-cis,13-trans-prostadienoic acid, which was separated into more polar and less plar epimers on preparative thin layer chromatography, $R_F$ = 0.15 and 0.30 respectively (3% acetic acid in ethyl acetate). The mass spectrum of the more polar isomer had M⁺ = 736.3598 (calculated for $C_{37}H_{65}ClO_5Si_4$ = 736.3562).

The starting material was prepared by the process described in the second part of Example 2 using (4-carboxy-3-methylbutyl)triphenylphosphonium bromide in place of (4-carboxybutyl)triphenylphosphonium bromide, via the following intermediates:

7-[2β-dimethoxymethyl-5α-hydroxy-3α-(tetrahydropyran-2-yloxy)cyclopent-1α-vl]-2-methyl-5-cis-heptenoic acid, $R_F$ = 0.26 (5% methanol in methylene chloride), n.m.r. in deuterated chloroform:
δ1.1–1.2, 3H, doublet, C<u>H</u>₃—CH<, 3.35, 6H, singlet, —CH(OC<u>H</u>₃)₂.

Methyl 7-[2β-dimethoxymethyl-5α-hydroxy-3α-(tetrahydropyran-2-yloxy)cyclopent-1α-vl]-2-methyl-5-cis-heptenoate, $R_F$ = 0.33 (5% methanol in methylene chloride), n.m.r. in deuterated chloroform:
δ1.1–1.2, 3H, doublet, C<u>H</u>₃.CH<,
3.35, 6H, singlet, —CH(OC<u>H</u>₃)₂,
3.65, 3H, singlet, —COOC<u>H</u>₃.

Methyl 7-[2β-dimethoxymethyl-5α-(4-phenylbenzoyloxy)-3α-(tetrahydropyran-2-yloxy)cyclopent-1α-vl]-2-methyl-5-cis-heptenoate, $R_F$ = 0.55 (ether), n.m.r. in deuterated chloroform:
δ0.9–1.1, 3H, C<u>H</u>₃—CH<,
3.4, 6H, —CH(OC<u>H</u>₃)₂,
3.6, 3H, —COOC<u>H</u>₃,
7.2—8.3, 9H, aromatic protons.

Methyl 7-[2β-dimethoxymethyl-3α-hydroxy-5α-(4-phenylbenzoyloxy)cyclopent-1α-yl]-2-methyl-5-cis-heptenoate, $R_F$ = 0.42 (ether), n.m.r. in deuterated chloroform:
δ0.9–1.2, 3H, C<u>H</u>₃CH<,
3.4, 6H, —CH(OC<u>H</u>₃)₂, 3.6, 3H, —COOC$\underline{H}_3$.

Methyl 7-[2β-formyl-3α-hydroxy-5α-(4-phenylbenzoyloxy)-cyclopent-1α-vl]-2-methyl-5-cis-heptenoate, $R_F = 0.48$ (ether).

Methyl 15-(5-chloroindan-2-yl)-11α-hydroxy-2-methyl-15-oxo-9α-(4-phenylbenzoyloxy)-16,17,18,19,20-pentanor-5-cis,13-trans-prostadienoate, $R_F = 0.4$ (20% ethyl acetate in methylene dichloride), n.m.r. in deuterated chloroform (δ values):
1.0, 3H, doublet C$\underline{H}_3$—CH<,
3.15–3.22, 4H, multiplet, indane C1 & C3 protons,
3.58, 3H, singlet, —CO$_2$C$\underline{H}_3$.

Methyl 15-(5-chloroindan-2-yl)-11α,15-dihydroxy-2-methyl-9α-(4-phenylbenzoyloxy)-16,17,18,19,20-pentanor-5-cis,13-trans-prostadienoate, $R_F = 0.1$ (20% ethyl acetate in methylene dichloride).

EXAMPLE 9

The process described in the first part of Example 8 was repeated using methyl 15-(5-chloro-2,3-dihydrobenzo[b]fur-2-yl)-11α,15-dihydroxy-2-methyl-9α-(4-phenylbenzoyloxy)-16,17,18,19,20-pentanor-5-cis,13-trans-prostadienoate as the starting material, to give the separated C-15 epimers of 15-(5-chloro-2,3-dihydro-benzo[b]-fur-2-yl)-9α,11α,15-trihydroxy-2-methyl-16,17,18,19,20-pentanor-5-cis,13-trans-prostadienoic acid, $R_F = 0.45$ and 0.50 respectively (3% acetic acid in ethyl acetate). The n.m.r. spectrum of each epimer in deuterated acetone showed the following characteristic features (δ values):
1.15, 3H, doublet, >CH—C$\underline{H}_3$,
3.21, 2H, doublet, dihydrofuryl C-3 protons,
3.8–4.4, 3H, multiplet, 3 —C$\underline{H}$(OH)—,
4.82, 1H, multiplet, dihydrofuryl C-2 proton,
5.2–5.8, 4H, multiplet, olefinic protons,
6.6–6.7, 3H, multiplet, aromatic protons.

The mass spectrum of the more polar epimer had $M^+ = 738.3392$ (calculated for $C_{36}H_{63}ClO_6Si_4 = 738.3391$)

The starting material used in the above preparation was prepared from methyl 7-[2β-formyl-3α-hydroxy-5α-(4-phenylbenzoyloxy)cyclopent-1α-yl]-2-methyl-5-cis-heptenoate by the process described in the latter part of Example 8, via the following intermediates:

Methyl 15-(5-chloro-2,3-dihydrobenzo[b]fur-2-yl)-11α-hydroxy-2-methyl-15-oxo-9α-(4-phenylbenzoyloxy)-16,17,18,19,20-pentanor-5-cis,13-trans-prostadienoate, $R_F = 0.8$ (50% ethyl acetate in toluene).

Methyl 15-(5-chloro-2,3-dihydrobenzo[b]fur-2-yl)-11α,15-dihydroxy-2-methyl-9α-(4-phenylbenzoyloxy)-16,17,18,19,20-pentanor-5-cis,13-trans-prostadienoate, $R_F = 0.1$ and 0.2 (ether).

EXAMPLE 10

To a solution of a mixture of C-15 epimers of methyl 15-(5-chloroindan-2-yl)-15-hydroxy-9α,11α-bis(4-phenylbenzoyloxy)-16,17,18,19,20-pentanor-5-cis,13-trans-prostadienoate (183mg., 0.227 mmole) in methanol (12ml.) containing 1,2-dimethoxymethane (4ml.) was added anhydrous potassium carbonate (125mg.), and the mixture was stirred at room temperature for 18 hours. The solution was adjusted to pH 7 with 1N hydrochloric acid and the solvent was evaporated in vacuo. The residue was treated with water (10ml.) and extracted with ethyl acetate (2 × 50ml.). The combined extracts were dried, the solvent was evaporated in vacuo, and the residue was chromatographed on preparative thin layer plates, developed in ethyl acetate, to give the separated C-15 epimers of methyl 15-(5-chloroindan-2-yl)-9α,11α,15-trihydroxy-16,17,18,19,20-pentanor-5-cis,13-trans-prostadienoate, $R_F = 0.2$ and 0.3 respectively (ethyl acetate). The mass spectrum had $M^+ = 664.3207$ (calculated for $C_{34}H_{57}ClO_5Si_3 = 664.3202$).

EXAMPLE 11

The process described in Example 10 was repeated using methyl 15-(2,3-dihydrobenzo[b]thien-2-yl)-15-hydroxy-9α,11α-bis(4-phenylbenzoyloxy)-16,17,18,19,20-pentanor-5-cis,13-trans-prostadienoate as the starting material, to give the separated C-15 epimers of methyl 15-(2,3-dihydro-benzo[b]thien-2-yl)-9α,11α,15-trihydroxy-16,17,18,19,20-pentanor-5-cis,13-trans-prostadienoate, $R_F = 0.30$ and 0.40 respectively (ethyl acetate). the mass spectrum had $M^+ = 648.3017$ (calculated for $C_{33}H_{56}O_5SSi_3 = 648.3068$).

The intermediate enone used in the process was obtained by the method given in note (m) of Example 5.

EXAMPLE 12

A solution of 9α,11α,15-trihydroxy-15-(2,3-dihydrobenzo[b]fur-2-vl)-16,17,18,19,20-pentanor-5-cis,13-trans-prostadienoic acid (5mg.) was dissolved in methanol (0.1ml.) and excess diazomethane was added at 0° C. The solvents were removed in vacuo to give a mixture of C-15 epimers of methyl 9α,11α,15-trihydroxy-15-(2,3-dihydrobenzo-[b]fur-2-yl)-16,17,18,19,20-pentanor-5-cis,13-trans-prostadienoate, $R_F = 0.3$ (ethyl acetate). The mass spectrum had $M^+ = 632.3344$ (calculated for $C_{33}H_{56}O_6Si_3 = 632.3385$).

EXAMPLE 13

To a solution of the more polar epimers of methyl 15-(5-chloroindan-2-yl)-9α,11α,15-trihydroxy-16,17,18,19,20-pentanor-5-cis,13-trans-prostadienoate (14mg.) in tetrahydrofuran (1ml.) and ether (3ml.) was added lithium aluminium hydride (24mg.). The mixture was stirred at room temperature for 1 hour, the excess of hydride was destroyed by the addition of water (1ml.), and the mixture was extracted with ethyl acetate to give 15-(5-chloroindan-2-yl)-16,17,18,19,20-pentanor-5-cis,13-trans-prostadien-1,9α,11α, 15-tetraol. $M^+ = 708,3618$ (calculated for $C_{36}H_{65}ClO_4Si_4 = 708.3648$), $R_F = 0.2$ (5% methanol in ethyl acetate).

EXAMPLE 14

| | % w/v |
|---|---|
| 15-(5-chloroindan-2-yl)-9α,11α,15-trihydroxy-16,17,18,19,20-pentanor-5-cis,13-trans-prostadienoic acid | 0.003 |
| Sodium phosphate B.P. | 2.90 |
| Sodium acid phosphate B.P. | 0.30 |
| Water for injection | to 100 |

The sodium phosphate B.P. was dissolved in about 80% of the water, followed by the prostadienoic acid derivative, and when dissolved, the sodium acid phosphate B.P. The solution was made up to volume with water for injection, and the pH was checked to be between 6.7 and 7.7. The solution was filtered to remove particulate matter, sterilised by filtration, and filled into pre-sterilised neutral glass ampoules under aseptic conditions. Immediately before use, the contents of an ampoule are diluted in sodium chloride B.P. for administration by intravenous infusion.

The prostadienoic acid derivative may, of course, be replaced by an equivalent amount of another prostanoic acid derivative of the invention.

EXAMPLE 15

The process described in Example 14 was repeated, omitting the sodium phosphate B.P. and sodium acid phosphate B.P., to give ampoules containing a sterile aqueous solution of 15-(5-chloroindan-2-vl)-9α,1-1α,15-trihydroxy-16,17,18,19,20-pentanor-5-cis,13-trans-prostadienoic acid, which are used in the manner described in Example 14.

The prostadienoic acid derivative may be replaced by an equivalent amount of another prostadienoic acid of the invention, to give other sterile aqueous solutions.

What we claim is:

1. A cyclopentane derivative of the formula:

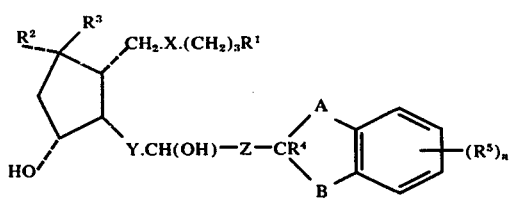

wherein $R^1$ is carboxy, hydroxymethyl or alkoxycarbonyl of up to 11 carbon atoms,
  $R^2$ is hydroxy or alkanoyloxy of 1 to 4 carbon atoms, and
  $R^3$ is hydrogen, or
  $R^2$ and $R^3$ together are oxo,
  X is ethylene or cis-vinylene,
  Y is ethylene or trans-vinylene,
  Z is a direct bond or alkylidene of 1 to 5 carbon atoms,
  A is alkylidene of 1 to 5 carbon atoms and
  B is oxygen,
  $R^4$ is hydrogen or alkyl of 1 to 4 carbon atoms, or $CR^4$ together with an adjacent carbon of A or B forms a double bond,
  $R^5$ is halogen or alkyl, alkoxy or halogenoalkyl each of 1 to 5 carbon atoms,
which compound bears 0 or 1 alkyl substituent of 1 to 4 carbon atoms on the trimethylene group, and for those compounds wherein $R^1$ is carboxy, the pharmaceutically or veterinarily acceptable base addition salts thereof.

2. The cyclopentane derivative of claim 1 wherein

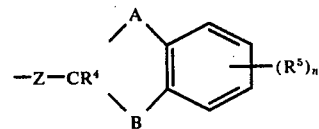

is 2-benzo[b]furyl or 2,3-dihydrobenzo[b]fur-2-yl, wherein $R^5$ and n are as defined in claim 1.

3. The cyclopentane derivative of claim 2 wherein
  $R^1$ is carboxy, methoxycarbonyl or hydroxymethyl,
  $R^2$ is hydroxy,
  $R^3$ is hydrogen, or
  $R^2$ and $R^3$ together are oxo,
  X is cis-vinylene,
  Y is trans-vinylene, and

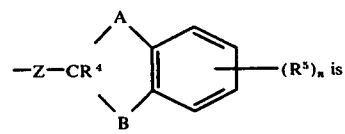

2-benzo[b]furyl, 2,3-dihydrobenzo[b]fur-2-yl, 5-chloro-2,3-dihydrobenzo[b]fur-2-yl, 2,3-dihydro-5-methoxybenzo[b]fur-2-yl or 2,3-dihydro-6-methoxybenzo[b]fur-2-yl, which compound bears 0 or 1 methyl substituent on carbon atom 2.

4. The cyclopentane derivative of claim 1 which has the formula:

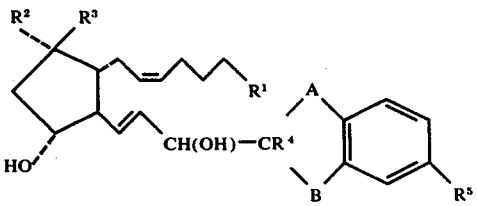

wherein $R^1$ is carboxy, methoxycarbonyl or hydroxymethyl, $R^2$ is hydroxy and $R^3$ is hydrogen or $R^2$ and $R^3$ together are oxo, $R^4$ is hydrogen or methyl, A is oxygen, B is methylene and $R^5$ is hydrogen, chlorine, bromine or methyl, and for those compounds wherein $R^1$ is carboxy, the pharmaceutically or veterinarily acceptable base addition salts thereof.

5. The cyclopentane derivative of claim 1 which is 15-(5-chloro-2,3-dihydrobenzo[b]fur-2-yl)-9α,1-1α,15-trihydroxy-16,17,18,19,20-pentanor-5-cis,13-trans-prostadienoic acid.

6. The cyclopentane derivative of claim 1 which is 15-(5-chloro-2,3-dihydrobenzo[b]fur-2-yl)-11α,15-dihydroxy-9-oxo-16,17,18,19,20-pentanor-5-cis,13-trans-prostadienoic acid.

7. A pharmaceutical or veterinary composition comprising an effective amount of the cyclpentane derivative of claim 1 together with a major amount of a pharmaceutically-or veterinarily-acceptable diluent or carrier.

* * * * *